June 18, 1974 S. L. COFFIN Plant Pat. 3,572
AZALEA PLANT (VOLUPTUOUS)
Filed April 23, 1973
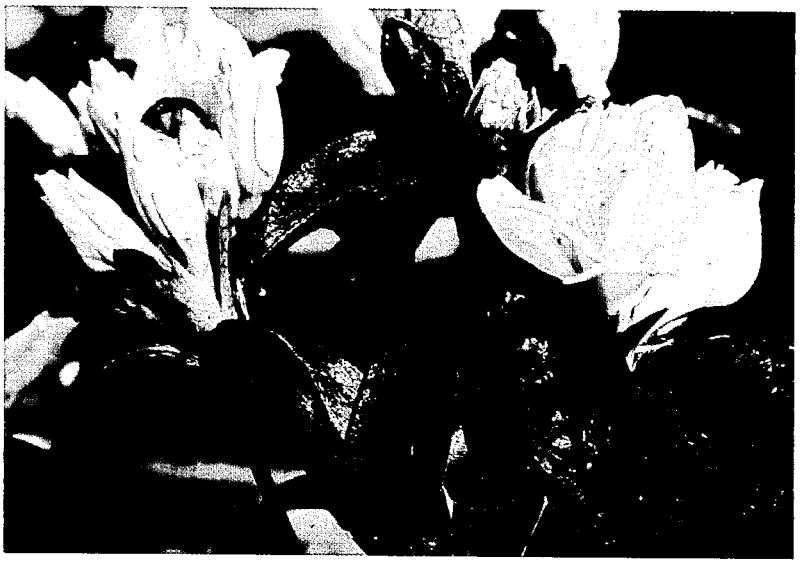
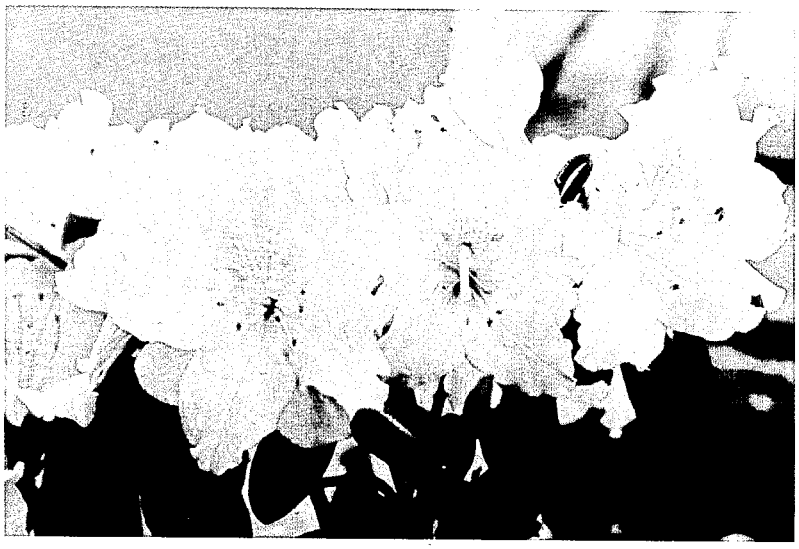

United States Patent Office

Plant Pat. 3,572

Patented June 18, 1974

3,572

AZALEA PLANT

Samuel L. Coffin, W. Four Ridge Road,
House Springs, Mo. 63051

Filed Apr. 23, 1973, Ser. No. 353,602
Int. Cl. A01h *5/00*
U.S. Cl. Plt.—56 1 Claim

ABSTRACT OF THE DISCLOSURE

A new variety of azalea, of the Kaempferi type, characterized by its more upright growth habit as compared with its seed parent Fedora (unpatented), its complete lack of seed production, and its resultant heavy blooming during each flowering season.

BACKGROUND OF THE INVENTION

My new variety of azalea plant originated as a seedling resulting from a cross of Fedora (unpatented) and Salmon Beauty (unpatented) made by me at House Springs, Mo., during the course of breeding efforts carried by me since 1962 with the object of producing a non-seeding variety having a better growth habit and which would otherwise retain the advantages of a popular variety such as Fedora. This seedling of Fedora appeared to have the characteristics that I was seeking and was therefore selected by me for propagation. Propagation of this new plant by cuttings has been carried on by me at House Springs, Mo., through several generations and all of its scions have shown that its novel characteristics are firmly fixed and hold true from generation to generation.

DESCRIPTION OF THE DRAWING

My new variety of azalea plant is illustrated by the accompanying photographic drawings in which the upper view shows the bud clusters and leaves and the lower view shows full opened blossoms, the colors shown being as nearly true as can be obtained by conventional photographic procedures.

DESCRIPTION OF THE NEW PLANT

The following is a detailed description of the new variety of azalea plant with color designations according to the R.H.S. Colour Chart produced under the direction of the British Colour Council and issued by the Royal Horticultural Society of London, England.

*The plant*

Origin: Seedling
Parentage: Seed parent—Fedora (unpatented). Pollen parent—Salmon Beauty (unpatented).
Classification: Botanic—Kaempferi. Commercial—Hardy, evergreen.
Form: Bush—Shape: Taller than broad.
Height: 6 feet or more
Trunk size: Bush—¾ to 1 inch at base. Tree—1 to 1½ inches.
Bark: 201A
Growth habit: Upright and strong with good growth rate.
Branches: Slightly upright and more closely spaced than Fedora.
Size: ¼ inch to ½ inch midway.
Bark: 200D, nearly smooth.
Foliage—leaves:
*Quantity.*—Generous
*Size.*—1½ to 2½ inches long, ¾ to 1¼ inches wide.
*Form.*—Elliptic or rhombic to ovate with nearly even margins. *Texture.*—Leathery, smooth on top and semi-glossy. *Pubescense distribution.*—Rufous hairs on midrib and petiole.

*Color.*—Upper side—138A. Under side—Lighter Green, in new growth 144A.
*Ribs and veins.*—Rather pronounced.

*Flower buds*

Form: Long.
Size: ⅜ to ½ inch in diameter and 1 to 1⅛ inch in length when petals are about to open.
Rate of opening: Quite fast and uniform.
Color: When sepals first divide—55D. When petals begin to unfurl—55B.
Sepals: Hooded over bud before opening. Spear shaped, and curl back slightly after breaking.
Color: Inside—Light Green. Outside—Same as leaves, 138A.
Calyx: Calyx splits and its aspect is smooth.
Peduncle: None. The bud is sessile.

*The flower*

Blooming period: About three weeks in midwest climate.
Quantity: Profuse.
Size: Medium. 2¼ to 2½ inches in diameter and 1¼ to 1¾ inches in depth including throat.
Borne: In cluster of two to five blossoms.
Shape: Cup shaped when first opening changing to hose-in-hose with two sets each with five petals.
Petalage: Number—10. Arrangement—imbricate.
*Form.*—Oval. Margin—Some are wavy.
*Color.*—Outer petal, body—55C. Inside petal, body—55C; spots and base—55B. Reverse side of petal—55C. When the flowers are fully mature, their background color is more nearly 55D with the blotches and throat about 55C. Colors will vary according to weather conditions and growing environment.
*Texture.*—Soft. Appearance—Satiny.
*Petaloids.*—None.
Peduncle: None. The flower is sessile.
Fragrance: None.

*Reproductive organs*

Stamens:
*Anthers.*—Five in number 1¼ to 1½ inches long arranged at bottom center of flower. Color—200B.
*Filaments.*—1¼ to 1⅜ inches long. Color—55C.
*Pollen.*—Sparse and whitish yellow in color.
Pistils: 1 to 1¼ inches in length. Color—55B.
*Stigmas.*—Color—200B.
Ovaries: Not visible.
Seeds: None.

Compared with its seed parent (Kaempferi "Fedora"), my new azalea plant has better form, sturdier growth and neater, more upright branch habit. This new variety has the hose-in-hose flower form of its pollen parent Salmon Beauty and since it does not produce seeds, as does Fedora, it blooms heavily each flowering season. Azaleas which produce many seeds fail to bloom well the following season unless the seeds are removed soon after the flowers have shattered.

This new variety has better foliage than ordinary Kaempferi types in that it has more evergreen leaves which are leathery and shiny and of a deeper green color. The flower buds are larger and longer, more freeze resistant, and capable of withstanding well below zero weather. The flowers have more variation in color, being of a Neyron Rose pink background with deeper Neyron Rose colored spots on the top petals and in the flower throat, producing a two-tone effect.

I claim:

1. A new and distinctive variety of azalea plant substantially as herein shown and described, characterized by profuse and seedless flowering, its abundant production of evergreen foliage, and its large flower buds which are more freeze resistant than usual in the Kaempferi azalea strain.

No references cited.

ROBERT E. BAGWILL, Primary Examiner